United States Patent [19]

Graham

[11] Patent Number: 4,750,498

[45] Date of Patent: Jun. 14, 1988

[54] METHOD AND TOOL FOR INSERTING AN INTRAOCULAR LENS

[75] Inventor: William M. Graham, Vashon Island, Wash.

[73] Assignee: CooperVision, Inc., Menlo Park, Calif.

[21] Appl. No.: 831,584

[22] Filed: Feb. 21, 1986

[51] Int. Cl.$^4$ .............................................. A61B 5/10
[52] U.S. Cl. ................................ 128/774; 128/303 R
[58] Field of Search ............... 128/774, 303 R; 623/6

[56] References Cited

U.S. PATENT DOCUMENTS

| | | | |
|---|---|---|---|
| 4,251,887 | 2/1981 | Anis | 128/303 R X |
| 4,279,259 | 7/1981 | Lee et al. | 128/774 |
| 4,319,564 | 3/1982 | Karickhoff | 128/774 |
| 4,349,027 | 9/1982 | Di Francesco | 128/303 R |
| 4,600,003 | 7/1986 | Lopez | 128/303 R |
| 4,600,004 | 7/1986 | Lopez et al. | 128/303 R |

Primary Examiner—Michael H. Thaler
Attorney, Agent, or Firm—Vorys, Sater, Seymour & Pease

[57] ABSTRACT

A method and channeled tool adapted for guiding an intraocular lens into position through an incision in an eye. Indicia means are provided in the tool in the form of two through-holes positioned at pre-determined distances from the distal end of the tool to determine the operable compression range of the intraocular lens haptics so that the surgeon can determine that the subject eye is of a sufficient size to receive the selected intraocular lens.

9 Claims, 2 Drawing Sheets

METHOD AND TOOL FOR INSERTING AN INTRAOCULAR LENS

BACKGROUND OF THE INVENTION

This invention relates to a method and tool for inserting an intraocular lens in an anterior chamber of an eye. More particularly, this invention relates to a tool having a planar member with a pair of longitudinally elongated channels for receiving the ends of haptics of an intraocular lens for guiding the lens into position in an eye. More particularly, this invention relates to such a tool having openings therein for determining whether a selected intraocular lens is an appropriate size for a subject eye. Still more particularly, this invention relates to a method for inserting an intraocular lens in an anterior chamber of the eye by inserting a tool into an incision in the eye, determining that the eye is appropriately sized to receive a given lens, inserting the given lens in channels in the tool, and moving the lens along the channels into position in the eye, and then withdrawing the tool from the incision while retaining the lens in the eye.

A number of surgical procedures are known for extracting an impaired lens, such as a cataractous lens of a human eye, removing the natural lens, and implanting an artificial lens within the eye. As is well known, an implant must be located either in the anterior chamber of the eye or in its posterior chamber. In such procedures, typically an incision is made in the eye, the affected impaired lens removed through the incision, and the implantable lens is inserted through the incision, and positioned within the eye so that it may be fixed therein, such as by suturing the lens or a haptic for the lens.

A variety of lens structures are known to facilitate fixing the lens within the eye by suturing at a location remote from a fixed lens position or by the use of haptic structures, such as loops, to stabilize a centralized optical zone of the lens once it is implanted. U.S. Pat. No. 4,251,887 discloses an example of a posterior chamber capsular lens implant and a method for implantation of the lens by the use of a tool in the form of a plastic sheet in the shape of a Sheet's Glide. A plastic sleeve is also shown having a diameter sufficient to retain the lens implant and rounded at one end. The sleeve is loaded with a lens implant immediately after extracapsular cataract extraction and the sleeve containing the lens implant is introduced, rounded end first, into the eye between preplaced sutures. The plastic sleeve is then withdrawn from the eye while leaving the lens implant in place in the eye for suturing.

U.S. Pat. No. 4,349,027 is another example of a tool for implanting an intraocular lens in the form of a guide having an elongated narrow plate with each edge rolled upwardly and inwardly to form flanges.

It has remained a problem in the art, however, to provide a simple and convenient tool for retaining an intraocular lens with the tool for ready insertion into an anterior chamber of an eye. An associated difficulty occurs in matching a given IOL size with the physical size of an eye undergoing lens replacement. A physician is thus interested in determining readily and easily whether an eye of a patient is of sufficient size to receive a pre-selected IOL having a given size.

Accordingly, it is an object of this invention to provide an insertion tool for assisting in the insertion of an intraocular lens in an anterior chamber of an eye.

It is another object of this invention to provide such a tool having mutually opposing channels structurally adapted to receive the ends of haptics of a particular style of intraocular lens having suitable transportable haptics for ready insertion of the implantable lens in an eye.

It is another object of this invention to provide such a tool with a blunted distal end for insertion through an incision at a location where the cornea meets the sclera and having indicia in the form of two through-holes positioned at pre-determined distances from the distal end of the tool to represent the operable compression range of the haptics on the intraocular lens so that the surgeon can determine that the eye is of a sufficient size to receive a pre-selected IOL by viewing the iris through a distal through-hole and the sclera through a proximal through-hole.

It is still another object of this invention to provide a method for inserting an intraocular lens into an eye by inserting a tool into an incision in an eye, inserting an intraocular lens in channels of a tool, moving the intraocular lens along the channels into position in the eye, retaining the lens in place in the eye while withdrawing the tool from the incision, and positioning the proximal haptic of the lens within the scleral spur within the eye.

It is still another object of this invention to provide in connection with such a procedure a readily observable method for determining that an eye size is appropriate for receiving a given lens through the use of structural features of the tool.

These and other objects will become apparent from the following written description of the invention.

BRIEF SUMMARY OF THE INVENTION

Directed to achieving the foregoing objects of the invention and overcoming problems in the art while providing a convenient method and tool for inserting an implantable intraocular lens into an eye, the invention comprises, in one aspect, a tool structurally adapted for receiving haptics of an intraocular lens. The tool includes an elongated planar member having a blunted distal end and defining a pair of opposed longitudinally elongated channels for receiving the haptics of the lens. The planar member member defines a pair of spaced openings at locations related to the blunted distal end of the tool so that when the tool is inserted through an incision in an eye where the cornea meets the sclera, the through-holes are respectively positioned at pre-determined distances from the distal end of the tool to represent the operable compression range of the haptics on the lenses. Thus, when the physician views the iris of the eye through the distal through-hole and sclera through the proximal through-hole, the eye measurements are correct for the particular lens.

The method according to the invention comprises the step of inserting a tool of the type described through an incision at the point where the cornea meets the sclera, viewing the portions of the eye through the spaced through-holes positioned relative to the blunted distal end of the tool to determine whether the eye is of sufficient size to receive a pre-selected IOL, inserting an intraocular lens in the channels in the tool, moving the lens into position in the eye by longitudinally translating the lens along the channel, retaining the lens in place within the eye while withdrawing the tool from the incision, positioning the proximal haptic within the scleral spur within the eye, and fixing the lens within the eye.

These and other objects and features of the invention will become apparent from the detailed description of the invention in its preferred embodiment which follows, taken in conjunction with the following drawings.

DETAILED DESCRIPTION OF THE PREFERRED EMBODIMENT

Figure 1:
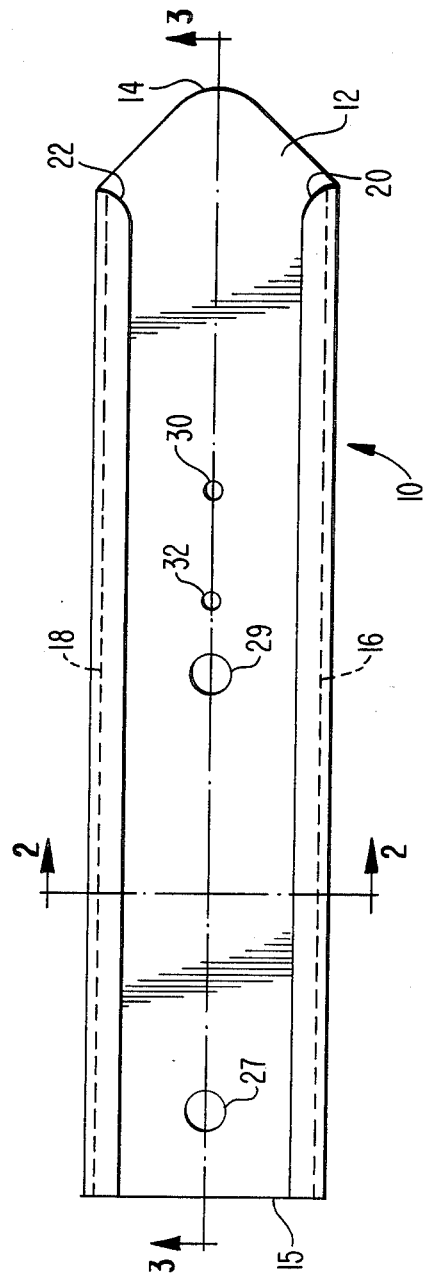
FIG. 1 is a top plan view of the insertion tool for an intraocular lens according to the invention.
Figure 3:
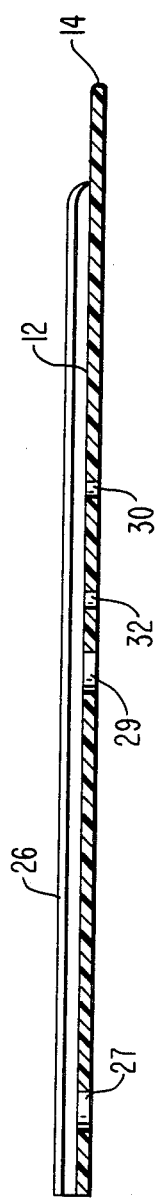
FIG. 3 is a side cross-sectional view taken along line 3—3 of FIG. 1.
Figure 2:
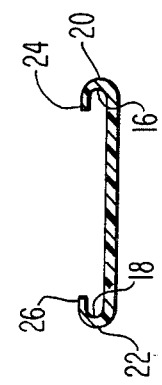
FIG. 2 is a cross-sectional view taken along line 2—2 of FIG. 1.

In FIG. 1, a tool for inserting an intraocular lens into an eye is designated generally by the reference numeral 10. The tool 10 includes an elongated planar member 12 defining a smooth upper surface 13 and a blunted, generally V-shaped, distal end 14 for insertion into an eye. Preferably, the tool 10 is tapered slightly toward its distal end 14. When the tool is inserted through an incision in the eye at a point where the cornea meets the sclera, or white portion of the eye, the blunted distal end 14 is located at the other diameter of the scleral spur.

The elongated planar member 12 of the lens insertion tool 10 defines a pair of opposed spaced channels 16 and 18 extending longitudinally substantially along the entire length of the planar member 12. The channels are respectively defined by curved outer members 20 and 22 which respectively terminate in inwardly-directed, rounded end portions 24 and 26 define the channel 16 and 18. The end portions 24 and 26 are located inwardly of the lateralmost portions of the tool and extend substantially longitudinally and in parallel to the centerline of the tool, while spaced upwardly slightly from the upper surface 13 of the planar member 12. The portions 20, 22, 24, and 26 thus structurally define the channels 16 and 18 which are structurally adapted for receiving the haptics of an intraocular lens of the type shown in FIGS. 4 and 5 in a secure relationship which permits free longitudinal movement of the haptics and optical zone of a lens along the surface 13, while securing the lens against lateral movement while positioned in the channels 16, 18 of the tool 10. The interiors of the channels 16 and 18 are smooth to permit the haptics of the intraocular lens to travel smoothly therealong for easy insertion into an eye as appropriate.

Preferably, the tools are made by a known process, such as injection molding, of a suitable polymer material such as polypropylene having a length of about 40 mm and a width of about 7 mm.

A pair of openings 27, 29 are provided in the planar member 12, generally nearer its proximal end 15 to permit drainage of sterile solution when a lens is placed on the tool 10 prior to insertion.

Figure 4:
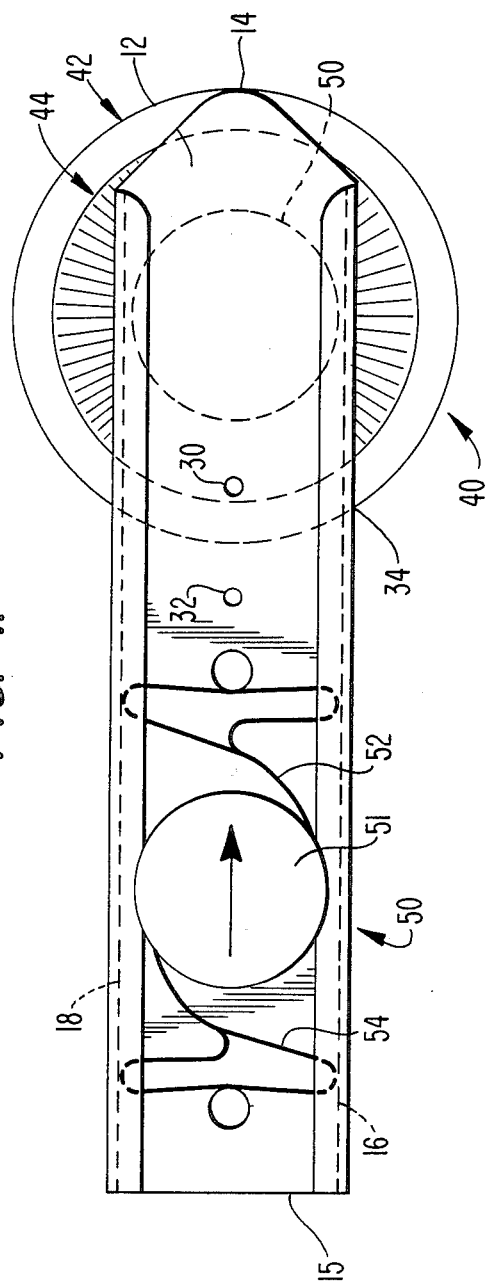
FIG. 4 is a top plan view of the tool according to the invention positioned within the eye and showing an intraocular lens loaded in the tool.

The planar member 12 further defines a distal through-opening 30 and a proximal through-opening 32, respectively located at pre-determined distances from the blunted distal end 14 of the tool 10. Preferably, the distal through-opening 30 is located at a distance of 11.5 mm from the distal end 14, while the proximal through-opening 32 is located at a distance of 13.5 mm from the blunted distal end 14. The through-openings 30 and 32 provide a convenient method for determining whether the eye is of sufficient size to receive a preselected IOL having a given size. As best seen in FIG. 4, when the tool 10 is inserted through an incision 34 in the eye and the blunted distal end 14 is located adjacent the scleral spur 42 of an eye 40, the through-hole 30 is located over the iris 44, while the through-opening 32 is located over the sclera 42. Thus, when the physician views the iris 44 through the distal opening 30, and the sclera through the proximal opening 32, the eye is appropriately sized. Thereafter, because the channels 16 and 18 are freely open to the exterior at the proximal end 15 of the tool 10, a lens 50 may be inserted into the channels 16 and 18 and moved into position in the eye. The channels 16 and 18 are mutually opposing and structurally adapted to receive the ends of haptics 52 and 54 of the lens 50 for the particular style of lens 50 shown in FIG. 4.

It may be thus understood that lenses of various sizes and various operable compression ranges are thus available to accommodate a wide range of eye sizes. Thus, preferably, a tool of the type described is provided with a lens wherein the tool is sized to accommodate that particular lens. In that case, the dimensions of the respective through-holes may vary from the preferred range stated to fit more precisely with a particular lens in the range of sizes of available lenses. Thus, in use, if the physician determines that iris shows through both openings 30, 32 for a preselected lens and its particular tool 10, he will immediately know that the preselected lens is too small and select a larger size lens. When he selects the large size lens, he may either merely insert it with its specialized tool 10, adapted to that larger lens, or follow the same procedure as outlined above to test whether the eye is correctly sized to receive the preselected large size lens. If, on the other hand, sclera appears through both openings for a particular preselected lens, he will know that the first preselected lens is too small, and select a smaller size lens based on that observation. In either case, an attempt to insert and incorrectly-sized lens and the resulting possibility that it may need to be removed from the chamber in favor of a correctly sized lens is avoided by the tool of the invention incorporating the gauge as described.

The tool is particularly adapted for securing the haptics of a CooperVision model 680 lens having an optical zone 51 and a pair of spaced, opposed haptics, 52, 54 having a lateral extent suitable for insertion in the spaced channels 16, 18. However, other types of lenses and varying haptic shapes may also be used with the tool shown, or the size of the channels altered to accommodate other haptics.

Figure 6:
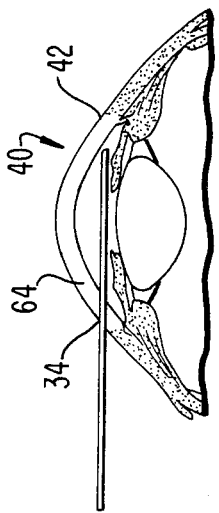
FIG. 6 is a diagrammatic size cross-sectional view of a portion of the eye showing the tool located within the eye through an incision for performing the method shown in FIGS. 4 and 5.
Figure 5:
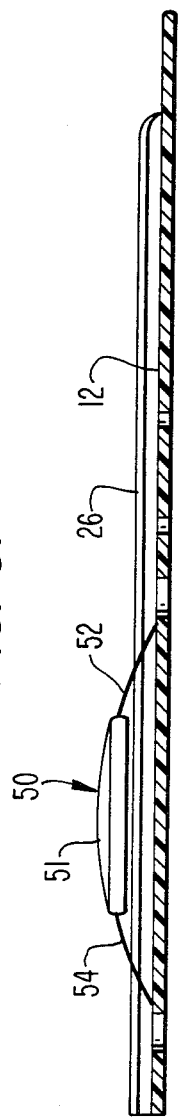
FIG. 5 is a side cross-sectional view of the tool according to the invention when loaded with an intraocular lens for insertion into an anterior chamber of the eye.

With the lens 50 positioned in the channels 16 and 18 as shown in FIGS. 4 and 5 and tool 10 positioned within the eye as shown in FIGS. 4 and 6, the lens 50 may be moved along the channels 16 and 18 into position within the eye 60. The lens 50 is then held in place within the eye 60 while the tool 10 is withdrawn from the incision 34. The proximal haptic 54 is then positioned within the scleral spur 42 and the procedure completed.

In the method according to the invention, as illustrated in FIGS. 4 and 6, an incision is first made in an eye 40 at a location where the cornea 64 meets the sclera 42. The tool 10 is then inserted with its blunted distal end 14 forward, into the incision 34 in the eye 40 to an extent where the distal end 14 contacts the scleral spur 42. When so positioned, the through-holes 30 and 32 are positioned as described in connection with FIG. 4. Since the distances of the holes 30 and 32 from the blunted distal end 14 represent the operable compression range of the haptics 52 and 54 for the intraocular lens 50, the inserting physician then determines, using the tool, whether the eye is of sufficient size to receive the intraocular lens 50. When the physician sees the iris 44 beneath the distal through-hole 30, and the sclera 42 through the proximal through-hole 32, the eye measurements are correct. When it is determined that the eye measurements are correct, the intraocular lens 50 is inserted into the channels 16 and 18 as shown in FIGS. 4 and 5 and moved longitudinally along the tool 10 into position in the eye. Thus, channels 16, 18 guide the haptics 52, 54 and thus the lens 50 into the desired position by movement along the top surface 13 of the tool 10. The structure of the tool 10 secures the lens 50 against lateral movement, while freely permitting longitudinal movement. The lens 50 is then held in place in the eye, while the tool 10 is withdrawn from the incision 34 leaving the lens 50 within the eye 40. The proximal haptic 54 is then positioned within the scleral spur 42 and the procedure completed.

This invention may be embodied in other specific forms without departing from its spirit or essential characteristics. For example, the structure of the channels in the preferred embodiment may be altered to accommodate particular haptics for particular lenses. The present embodiments are, therefore, to be considered in all respects as illustrative and not restrictive, the scope of the invention being indicated by the claims rather than by the foregoing description, and all changes which come within the meaning and range of the equivalence of the claims are therefore intended to be embraced therein.

What is claimed is:

1. A tool for assisting in insertion of an intraocular lens in an anterior chamber of an eye, comprising:
    an elongated body member defined by a relatively narrow width for insertion of said elongated body member in an incision in said eye, said body member defining a distal tip which is structurally adapted to be inserted in said chamber to a predetermined reference location in said anterior chamber in said eye, and a proximal end opposite said distal tip,
    a guide means cooperating with said elongated body member defining a channel, having spaced, opposed channel-defining members, which is structurally adapted to secure the distal tips of a haptic of an intraocular lens against lateral movement relative to said elongated body member, while permitting free longitudinal movement of said lens in a substantially uncompressed state in said channel so that a lens positioned therein is longitudinally guided by said channel as the lens is moved from a location outside said eye through said incision into said anterior chamber within said eye for implantation therein, said channel being open at both said distal end and said proximal end of said elongated body member and between said channel-defining members in the region of an optic of said lens so that said lens may be loaded in said channel at said free proximal end and dispensed from said channel at said free distal end, and
    said body member defining a distal through-opening and a proximal through-opening respectively located at pre-determined distances from the distal tip of said body member, said distal through-opening and said proximal through-opening providing relative to said eye a gauge for determining a range of eye size, and the distance between said distal and proximal through-openings being representative of the operable compression range of the haptics of the intraocular lens retained by said channel on said elongated body member.

2. The tool as set forth in claim 1 wherein said body member is an elongated substantially planar member, said channel being defined by opposed elongated flanges constituting said channel-defining members, extending longitudinally along said planar body member and spaced inwardly along the outermost edges of said planar member and outwardly of a surface plane of said planar member to define said haptic-receiving channel.

3. The tool as set forth in claim 2 wherein said tool defines a blunted distal end.

4. the tool as set forth in claim 1 wherein said body member is made from a polymer.

5. A tool for assisting in inserting an intraocular lens in an anterior chamber of an eye, comprising:
    an elongated body member defined by a relatively narrow width for insertion of said elongated body member in an incision in said eye, said body member defining a distal tip which is structurally adapted to be inserted in said anterior chamber to a predetermined reference location in said eye,
    said body member including a means for guiding a lens therealong for insertion into an anterior chamber of an eye, and
    said body member defining a distal through-opening and a proximal through-opening respectively located at pre-determined distances from the distal tip of said body member to provide a size-determining gauge for determining a range of sizes of said eye, the distance between said distal and proximal through-openings being representative of the operable compression range of haptics of a pre-determined intraocular lens.

6. The tool as set forth in claim 5 wherein said distal through-opening is located approximately 11.5 mm from said distal tip while said proximal through-opening is located about 13.5 mm from said distal tip.

7. The tool as set forth in claim 6, wherein said distal through-opening and said proximal through-opening are located so that when said distal tip is inserted in said chamber at a scleral spur of said eye, said distal opening lies above the iris of said eye while said proximal opening lies above the sclera of said eye to provide an indication that said eye is of sufficient size to receive a predetermined lens.

8. A method for inserting an intraocular lens in an anterior chamber of an eye with a tool of the type comprising an elongated body member defined by a relatively narrow width for insertion of said elongated body member in an incision in said eye, said body member defining a distal tip which is structurally adapted to be inserted in said anterior chamber to a predetermined reference location in said eye, channel means cooperating with said elongated body member, said channel means being structurally adapted to secure a haptic of an intraocular lens against lateral movement relative to said elongated body member while permitting free longitudinal movement along said elongated body member in said channel means so that a haptic of a lens located in said channel means outside said incision may be longitudinally translated along said channel means to a position within said eye, while an optic of said lens lies generally between the opposite sides of said channel means, said elongated body member having a pair of longitudinally-spaced through-holes thereon, comprising the steps of:

providing an incision at a location on an eye;

inserting said elongated body member with said distal tip forward into said incision;

determining, when said distal tip is in the eye, by looking through said through-holes whether the eye is of sufficient size to receive the predetermined intraocular lens having a predetermined size;

moving said lens along said channel means into position in the eye;

retaining the lens in position in said chamber in said eye, while withdrawing said elongated body member from said incision; and positioning the proximal haptic of said lens within said eye.

9. The method as set forth in claim 8 wherein said inserting comprises inserting said elongated body member into said incision so that said distal tip contacts the scleral spur.

* * * * *